United States Patent
Takahashi et al.

(10) Patent No.: US 12,396,934 B2
(45) Date of Patent: Aug. 26, 2025

(54) POWDER COSMETIC

(71) Applicant: JO Cosmetics Co., Ltd., Tokyo (JP)

(72) Inventors: Fumiya Takahashi, Tokyo (JP); Kiho Gawahara, Tokyo (JP); Ikuo Kondo, Tokyo (JP); Hiroshi Shima, Tokyo (JP)

(73) Assignee: JO Cosmetics Co., Ltd., Tokyo (JP)

( * ) Notice: Subject to any disclaimer, the term of this patent is extended or adjusted under 35 U.S.C. 154(b) by 803 days.

(21) Appl. No.: 17/610,727

(22) PCT Filed: May 7, 2020

(86) PCT No.: PCT/JP2020/018488
§ 371 (c)(1),
(2) Date: Nov. 12, 2021

(87) PCT Pub. No.: WO2020/230682
PCT Pub. Date: Nov. 19, 2020

(65) Prior Publication Data
US 2022/0218576 A1    Jul. 14, 2022

(30) Foreign Application Priority Data
May 14, 2019   (JP) ................................. 2019-091150

(51) Int. Cl.
| | | |
|---|---|---|
| A61K 8/29 | (2006.01) | |
| A61K 8/02 | (2006.01) | |
| A61K 8/19 | (2006.01) | |
| A61K 8/25 | (2006.01) | |
| A61K 8/27 | (2006.01) | |
| A61K 8/87 | (2006.01) | |
| A61K 8/92 | (2006.01) | |
| A61Q 1/02 | (2006.01) | |

(52) U.S. Cl.
CPC .............. *A61K 8/29* (2013.01); *A61K 8/0241* (2013.01); *A61K 8/19* (2013.01); *A61K 8/25* (2013.01); *A61K 8/87* (2013.01); *A61K 8/922* (2013.01); *A61Q 1/02* (2013.01); *A61K 2800/432* (2013.01); *A61K 2800/436* (2013.01)

(58) Field of Classification Search
None
See application file for complete search history.

(56) References Cited

U.S. PATENT DOCUMENTS

| | | | |
|---|---|---|---|
| 5,690,916 A | 11/1997 | Kimura et al. | |
| 8,252,298 B2* | 8/2012 | Maderazzo | A61Q 1/02 |
| | | | 424/70.13 |
| 8,703,162 B2 | 4/2014 | Nakamura et al. | |
| 9,655,835 B2* | 5/2017 | Finjan | A61Q 1/12 |
| 2008/0226574 A1 | 9/2008 | Thevenet | |

FOREIGN PATENT DOCUMENTS

| | | | |
|---|---|---|---|
| JP | S63196505 A | | 8/1988 |
| JP | H0881333 A | | 3/1996 |
| JP | H10194912 A | * | 7/1998 |
| JP | 2001199840 | * | 7/2001 |
| JP | 2001199840 A | | 7/2001 |
| JP | 2004315426 A | | 11/2004 |
| JP | 3697428 B2 | | 9/2005 |
| JP | 2008127388 A | | 6/2008 |
| JP | 2011225563 A | | 11/2011 |
| JP | 2015193552 A | | 11/2015 |
| JP | 5916949 | * | 5/2016 |
| JP | 2018135385 A | * | 8/2018 |
| KR | 101935647 | * | 1/2017 |

OTHER PUBLICATIONS

English Abstract for JP2015193552 A, Nov. 5, 2015.
English Abstract for JP63196505 A, Aug. 15, 1988.
English Abstract for JP081333 A, Jan. 9, 1996.
English Abstract for JP10194912 A, Jul. 28, 1998.
English Abstract for JP2001199840 A, Jul. 24, 2001.
English Abstract for JP2004315426 A, Nov. 11, 2004.
English Abstract for JP3697428 B2, Sep. 21, 2005.
English Abstract for JP2008127388 A, Jun. 5, 2008.
English Abstract for JP2011225563 A, Nov. 10, 2011.

* cited by examiner

*Primary Examiner* — Danah Al-Awadi
(74) *Attorney, Agent, or Firm* — CAHN & SAMUELS, LLP

(57) ABSTRACT

A powder cosmetic comprising 3 to 80% by mass of a colorless interference pigment having a chroma C* of 5.0 or more (A), and 0.001 to 3% by mass of a color pigment (B), wherein a hue difference value ΔH* between an appearance color and a coating color is 10 or more is provided. The powder cosmetic may contain a content of 40 to 96% by mass of an inorganic extender pigment (C), a content of 1 o 30% by mass of an organic extender pigment (D), and a content of 1 to 30% by mass of an oily component (E).

15 Claims, No Drawings

POWDER COSMETIC

This application is a U.S. national stage application of PCT/JP2020/018488 filed on 7 May 2020 and claims priority to Japanese patent document 2019-091150 filed on 14 May 2019, the entireties of which are incorporated herein by reference.

TECHNOLOGICAL FIELD

The present invention relates to a powder cosmetic having a different color tone between an appearance color of the cosmetic and a color of a cosmetic film after being applied to the skin, and more specifically to a powder cosmetic suitable as a makeup cosmetic for skin color correction.

BACKGROUND TECHNOLOGY

In makeup cosmetics, finishing of a cosmetic film after application such as vivid color development, gloss, and stereoscopic effect of the cosmetic film is an important element of attractiveness of a product. Besides, a visual presentation at the time of application is also one of the attractiveness. Here, the term "visual presentation" means that a cosmetic film having a color tone different from an appearance color of the cosmetic itself is obtained by applying the cosmetic to the skin. As to such a cosmetic aiming to have the visual presentation, for example, patent document 1 discloses a makeup cosmetic containing a compression-collapsed soft resin capsule including at least one component selected from a color pigment, a colored nacreous pigment and an oil-soluble dye, and an oily component. In this cosmetic, an application color can be controlled by a degree of application force when applied to the skin and the number of times of rubbing, so that the cosmetic has an advantage that users can enjoy a makeup by changing an application color in accordance with a change of their preference, a change of their skin color, or their mood of the day, or by changing an application color for each part of the face.

In addition, patent document 2 discloses a water-in-oil cosmetic containing a soft aggregated particle composed of a water-soluble polymer containing carrageenan and/or xanthan gum and an inorganic colorant in an inner aqueous phase. In this cosmetic, the cosmetic is rubbed on the skin to develop a color, and a cosmetic film having a color tone different from an appearance color of the cosmetic itself can be formed on an application site.

In the case of the cosmetic described in the patent document 1, coloring of the cosmetic film is caused by making to disperse a color pigment, which is contained in a soft resin capsule, in the cosmetic film via collapse of the soft resin capsule. Therefore, the cosmetic applied to the skin must be strongly rubbed to disintegrate the soft resin capsule, so that the cosmetic has a defect that a film of the collapsed capsule remains on the skin to impair spreadability of the cosmetic or tends to cause to generate a crease. In the case of the cosmetic described in the patent document 2, a soft aggregated particle of an inorganic color pigment is required to be dispersed in an aqueous phase, so that this technology is difficult to apply to a powder cosmetic containing no water, and further, the cosmetic has a defect that transparency of a cosmetic film is impaired because the inorganic color pigment is included.

There are various types of makeup cosmetics according to their use. A skin color correction cosmetic is known as one example of the makeup cosmetics. This is also referred to "control color." This is a product that aims to adjust a skin color of a trouble such as a bias of skin color tone to a natural skin color by mainly utilizing a complementary color relationship. Conventionally, the skin color correction cosmetic was intensively developed. For example, patent document 3 discloses a skin color adjustment method for making a dark color part of the skin inconspicuous by using a substance having an interfering light and appropriately adjusting a wavelength of a transmitted interfering light. In this document, iron oxides-coated mica and titanium dioxide-coated mica are described as a blue interfering light material that transmits a yellowish light and a reddish light (See Examples 1 and 2)

Patent document 4 discloses a skin color adjusting agent containing a colored titanium dioxide-coated mica in which an iron oxide is coated on (titanium dioxide-coated mica), and that the colored titanium dioxide-coated mica is blended to prepare an oily compact foundation for correcting a blue dark color portion (see Example 3). The foundation contains, in addition to 20% by weight of a material having an interfering light, 11% by weight of titanium dioxide, 0.4% by weight of Red No. 226, 1.6% by weight of yellow iron oxide as a color pigment, and about 50% by weight of an oily component such as a wax, decamethylcyclopentasiloxane, squalane, and cetyl 2-ethylhexanoate.

Patent document 5 discloses a cosmetic additive for making a good-looking skin color that individuals originally had. The cosmetic additive is composed of titanium dioxide-coated mica that is further coated with a red organic dye. The document discloses, as a specific example, a foundation containing 10% by weight of titanium dioxide-coated mica coated with carmine that is a red organic dye, and in addition, as a color pigment, 8% by weight of titanium dioxide, 0.5% by weight of red iron oxide, 1.5% by weight of yellow iron oxide, 0.2% by weight of black iron oxide, and as an extender pigment, 29.5% by weight of talc, 35% by weight of sericite, and 5% by weight of mica (see Example 3). The document discloses that when titanium dioxide-coated mica coated with a red inorganic pigment (red iron oxide) is used instead of the titanium dioxide-coated mica coated with a red organic dye, the good-looking skin that individuals originally had cannot be obtained (see Comparative Example 3 and paragraph 0043).

A skin color correction cosmetic, which is also referred to "control color", has different characteristics depending on an interfering light material contained therein. It is generally known that a skin color correction cosmetic containing a green or blue interfering light material is effective in correcting redness of the skin, that a skin color correction cosmetic containing a violet or pink interfering light material is effective in correcting paleness of the skin, and that a skin color correction cosmetic containing a yellow or beige interfering light material is effective in correcting darkening, dullness, etc. of the skin. An interference color appears by applying and orienting an interfering light material such as titanium dioxide-coated mica on the skin. In the case of the cosmetics described in the above patent documents 3 to 5, they contain an interfering light material in which an inorganic or organic pigment is coated on its surface and also contain more than 10% by weight of a color pigment, so that, even when an interfering light of the interfering light material appears on the skin, an interference color is affected by a color tone of the inorganic pigment or organic pigment present on the surface of the interfering light material and the color pigment contained in a large amount. Hence, there are problems that it is difficult to make a significant change between a color tone of a cosmetic itself and a color tone of its cosmetic film and that transparency of the cosmetic film is impaired due to the color pigment contained in a large amount.

PRIOR ART DOCUMENT

Patent Document

Patent Document 1: JP-A S63-196505
Patent Document 2: JP-A 2011-225563
Patent Document 3: JP-A H08-81333
Patent Document 4: JP-B 3,697,428
Patent Document 5: JP-A 2004-315426

DISCLOSURE OF THE INVENTION

Problem to be Solved by the Invention

The present invention was completed under the aforementioned background art, and an object of the present invention is to provide a cosmetic having an aesthetic fun that a coating color different from an appearance color of the cosmetic itself appears, and a skin color correction effect without impairing transparency.

Means Used to Solve the Problem

As a result of intensive studies to develop a powder cosmetic having a coating color different from an appearance color of a cosmetic itself, the present inventors found that when a colorless interference pigment with a high chroma is used with a small amount of a color pigment in combination, a powder cosmetic having an aesthetic effect and a natural skin color correction effect can be obtained. The present invention was completed based on the above knowledge.

Thus, the present invention provides a powder cosmetic containing 1 to 60% by mass of a colorless interference pigment having a chroma C* of 5.0 or more (A), and 0.001 to 3% by mass of a color pigment (B), wherein a hue difference ΔH* between an appearance color and a coating color is 10 or more.

Effect of the Invention

The powder cosmetic of the present invention provides a cosmetic film having a coating color (color of a cosmetic film formed after application) different from its appearance color, and has an effect of correcting a skin color to a natural skin color when used as a skin color correction cosmetic. Further, since a color tone of a cosmetic can be imparted by a small amount of a color pigment while a color tone of a cosmetic film can be adjusted by an interference color of an interference pigment, a cosmetic having a color tone similar to that of a user's skin trouble can easily be prepared. For example, in order to correct redness of the skin, a cosmetic containing an interference pigment that provides a green or blue coating color is effective. In this case, the cosmetic can have an appearance color with a color tone similar to that of a user's skin trouble by blending a red or pink organic pigment, so that a user having no sufficient makeup knowledge can appropriately select a skin color correction cosmetic.

EMBODIMENT FOR CARRYING OUT THE INVENTION (A) Interference Pigment

An interference pigment of the component (A) used in the present invention is colorless and exhibits an interference color when oriented on the skin by application. The interference pigment may be a common material used in cosmetics as far as it meets the above definition. Particularly, a plate-like laminate referred to "pearl agent" that gives an interference color is preferably used. The plate-like laminate has a property of emitting a strong light from a layer composed of a metal oxide called an interference layer provided on a substrate such as mica, a glass flake, and a silica flake. The interference layer may be a single layer or a plurality of layers with different refractive indices. When composed of a plurality of layers, a refractive index difference between each layer is usually 0.3 to 2, preferably 0.5 to 1.

Specific examples of the interference pigment include titanium dioxide-coated mica, titanium dioxide-coated synthetic mica, titanium dioxide-coated glass flakes, titanium dioxide-coated silica flakes, (titanium dioxide and silicon oxide)-coated mica. The interference pigment preferably has a coating layer that contains titanium or titanium dioxide. Further, the interference pigment is preferably a plate-like powder.

The interference pigment of the component (A) used in the present invention is required to strongly exhibit an interference color because it is used to aim color the skin or to correct a skin color. From this viewpoint, a chroma C* value measured by the following method is required to be 5.0 or more. The chroma C* value is preferably 6.0 or more, more preferably 8.0 or more. When the chroma C* value is less than 5.0, a desired interference color cannot be obtained due to an influence of a color tone of a color pigment even if an interference color appears.

Chroma of Interference Pigment

Using a color meter (Color Whiteness Meter NW-12, manufactured by Nippon Denshoku Industries Co., Ltd.), a chroma C* value of a coating film obtained by applying an interference pigment in an amount of 1 mg/cm$^2$ on a black artificial skin (BIOSKIN PLATE #B, manufactured by Beaulax Corporation) is measured. Chroma C* is defined in CIE 1976L*a*b* color system and is represented by C*=$(a^{*2}+b^{*2})^{1/2}$.

A content of the interference pigment of the component (A) is 3 to 80% by mass, preferably 5 to 60% by mass, more preferably 10 to 50% by mass based on the total amount of the cosmetic. When the content of the interference pigment is excessively small, it is impossible to obtain a cosmetic film having a color tone different from an appearance color of a cosmetic, and when it is excessively large, finishing of a cosmetic film becomes unnatural.

A volume average particle diameter of the interference pigment of the component (A) used in the present invention is preferably 1 to 300 μm, more preferably 3 to 100 μm, further more preferably 5 to 60 μm. When the volume average particle diameter is smaller than this range, transparency of the cosmetic tends to decrease. Conversely, when the volume average particle diameter is larger than this range, chroma of a cosmetic film tends to decrease. An interference color of the interference pigment may be selected as appropriate. For example, the interference color may be any one of red, yellowish red, yellow, yellowish green, blue green, blue, blue-violet, and violet.

Here, the term "interference pigment" of the component (A) does not include a composite in which an inorganic pigment or an organic pigment is coated, as a coloring component, on a surface of a substrate. An example of such a composite is iron oxides-coated (titanium dioxide-coated mica). So-called a colored pearl such as iron oxides-coated (titanium dioxide-coated mica) is unable to provide a change of color tone between a cosmetic itself and its cosmetic film because a color tone of the cosmetic itself is sustained in the cosmetic film. Thus, such a colored pearl is treated as a color pigment of the component (B) described below.

Examples of a commercial product of the interference pigment of the component (A) include a series of HELIOS R10 (average particle diameter of 10 μm), a series of HELIOS R20 (average particle diameter of 20 μm), a series of HELIOS R100 series (average particle diameter of 100 μm), any of which is manufactured by Topy Industries and is titanium dioxide-coated synthetic fluorphlogopite; a series of METHASHINE 1040 (average particle diameter of 40 μm), a series of METHASHINE 1080 (average particle diameter of 80 μm), any of which is manufactured by Nippon Plate Glass Co., Ltd. and is a flake of titanium dioxide-coated glass; a series of FLAMENCO (average particle diameter of 25 μm), a series of FLAMENCO Satin (average particle diameter of 6 μm), any of which is manufactured by BASF and is titanium dioxide-coated mica, TIMMILON Super Red and Super Blue (average particle diameter of 10 to 60 μm), any of which is manufactured by Merck and is titanium dioxide-coated mica; and the like.

(B) Color Pigment

In the present invention, a color pigment of the component (B) is used to impart an appearance color tone to the powder cosmetic of the present invention. Color pigments are water-insoluble and oil-insoluble powders and are broadly classified into an inorganic pigment and an organic pigment. Examples of the inorganic pigment include inorganic white pigments such as titanium dioxide and zinc dioxide; inorganic red pigments such as red iron oxide (red iron) and iron titanate; inorganic brown pigments such as gamma-iron oxide; inorganic yellow pigments such as yellow iron oxide and ochre; inorganic black pigments such as black iron oxide and carbon black; inorganic violet pigments such as manganese violet and cobalt violet; inorganic green pigments such as chromium oxide, chromium hydroxide, cobalt titanate; and inorganic blue pigments such as Prussian blue and ultramarine.

The organic pigment may be a synthetic material or a naturally-derived material, and may be a material which is insoluble in itself or a material made insoluble by forming a lake of a water-soluble or oil-soluble dye. Examples of the organic pigment include Red No. 201, Red No. 202, Red No. 204, Red No. 205, Red No. 220, Red No. 226, Red No. 228, Red No. 405, Orange No. 203, Orange No. 204, Yellow 401 and Blue 404; lakes formed by a metal such as zirconium, barium and aluminum with a water-soluble dye such as Red No. 3, Red No. 104, Red No. 106, Red No. 227, Red No. 230, Red No. 401, Red No. 505, Orange No. 205, Yellow No. 4, Yellow No. 5, yellow No. 202, yellow No. 203, green No. 3, and blue No. 1; natural dyes and their lakes.

The color pigment preferably has a high tinting strength and a low hiding power because a coating color of a cosmetic film is desired not to be affected by a color of the color pigment. In this respect, since the organic pigment has a high tinting strength and a low hiding power compared with the inorganic pigment, it has a technical feature that, while it exhibits a vivid color in a state of a powder cosmetic, when a thin film such as a cosmetic film is formed, the thin film has almost no color since a blending amount of the organic pigment is small. Therefore, it is advantageous to use the organic pigment as the color pigment. Examples of preferred organic pigments include Red No. 201, Red No. 202, Red No. 226, Yellow No. 205, Yellow No. 401, Blue No. 404, aluminum lake of Yellow No. 4, aluminum lake of Yellow No. 5, and aluminum lake of Blue No. 1.

A content of the color pigment of the component (B) is 0.001 to 3% by mass, preferably 0.005 to 2% by mass, more preferably 0.01 to 1% by mass relative to the whole amount of the cosmetic in view of imparting an appearance color without affecting a coating color. When using the color pigment in an amount outside of this range, a degree of color tone difference between the appearance color and the coating color is reduced, and fun of the color tone change is lost. When the color pigment of the component (A) is a lake of an organic dye, the term "content of the color pigment" means a content of the organic dye excluding a laking agent (which is an agent used to make a lake) such as aluminum hydroxide.

The powder cosmetic of the present invention has an advantage that the color tone of the cosmetic before use (appearance color) is different from the color tone of the cosmetic film obtained when applied to the skin (coating color). Thus, users can obtain surprise and pleasure during makeup. When the cosmetic is used for skin color correction, if the cosmetic has an appearance color having a similar color tone to that of a skin trouble such as redness, yellow dullness and paleness of the skin, while containing an interference pigment giving an interference color that is a complementary color which can correct the color tone of the skin trouble, users can easily select an appropriate skin color correction cosmetic without any knowledge of makeup.

For example, a user who desires to correct redness of the skin may select a cosmetic that contains an interference pigment giving a blue-green interference color and has a reddish appearance color such as a pink color that is near to a color tone of the skin trouble. A user who desires to correct paleness of the skin may select a cosmetic that contains an interference pigment giving an orangish interference color and has a bluish appearance color. A user who desires to correct yellow dullness of the skin may select a cosmetic that contains an interference pigment giving a pinkish or purplish interference color and has a yellow appearance color. Thus, since the powder cosmetic of the present invention has an appearance color near to a color tone of a skin trouble, users can easily select an appropriate skin color correction cosmetic without any knowledge of makeup.

The powder cosmetic of the present invention has a hue difference value $\Delta H^*$ between an appearance color and a coating color is 10 or more, preferably 12 or more, and more preferably 15 or more. The larger the hue difference value, the greater enjoying of making up is obtained.

The hue difference value $\Delta H^*$ between an appearance color and a coating color can be measured by the following method.

Appearance Color:

A plate-like sample having a thickness of about 4 mm is prepared by filling 10 g of a powder cosmetic in a round metal pan having a depth of 4.5 mm and an inner diameter of 54 mm, and compression-molding the powder cosmetic at a pressure of 3 MPa using a hydraulic compression molding machine. Using a color meter (Color Whiteness Meter NW-12 manufactured by Nippon Denshoku Industries Co., Ltd.), a surface color of the plate-like sample is measured to determine L*, a*, b*, C* and a hue value H of Munsell.

Coating Color:

Using a color meter (Color Whiteness Meter NW-12 manufactured by Nippon Denshoku Industries Co., Ltd.), a color of a coating film obtained by applying a powder cosmetic on a black artificial skin (BIOSKIN PLATE #BK available from Beaulax Corporation) in amount of 2 mg/cm² is measured to determine L*, a*, b*, C* and a hue value H of Munsell. A hue difference value (ΔH*) between an appearance color and a coating color is determined based on the obtained measurement values above. The hue difference ΔH* is defined in CIE 1976*a*b* color system and is calculated by the following equation.

$$\Delta H^* = (\Delta a^{*2} + \Delta b^{*2} - \Delta C^{*2})^{1/2}$$

In the present invention, the powder cosmetic preferably contain an inorganic extender pigment (C) and/or an organic extender pigment (D) in addition to the component (A) and the component (B). Examples of the inorganic extender pigment to be used include fine particle titanium dioxide, fine particle zinc dioxide, talc, white mica, synthetic phlogopite, phlogopite, black mica, synthetic mica, sericite, zeolite, kaolin, bentonite, clay, silica, magnesium silicate, aluminum magnesium silicate, calcium silicate, barium sulfate, magnesium sulfate, calcium sulfate, calcium carbonate, magnesium carbonate, boron nitride, alumina, hydroxyapatite, and complexes thereof. Of these, boron nitride, sericite, and synthetic mica are excellent in usability and are preferably used.

A surface of these inorganic extender pigments is preferably hydrophobized in view of usability and long-lasting of makeup. Such surface-hydrophobized treatments may be performed according to conventional known methods. Examples of the method include baking treatment with a silicone such as methylhydrogenpolysiloxane and (dimethicone)/(methicone) copolymer; treatment with a fatty acid such as stearic acid; treatment with a fatty acid metal soap such as aluminum stearate and zinc stearate; acylatedamino acid treatment; lipoamino acid treatment which is a combination of the acylatedamino acid (salt) treatment and the fatty acid (salt) treatment; treatment with a fluorine compound such as perfluoroalkylphosphate; silylation treatment by trimethylsilane etc.; and acidic ester treatment by isostearyl sebacate etc. Of these, the acidic ester treatment, the acylatedamino acid treatment or the lipoamino acid treatment is particularly preferred in view of usability and long-lasting of makeup. A preferred example of the inorganic extender pigment is an isostearyl sebacate-treated talc. A content of the inorganic extender pigment may be appropriately selected. It is preferably 40 to 96% by mass, more preferably 45 to 90% by mass, more preferably 50 to 80% by mass based on the total amount of the powder cosmetic.

Examples of the organic extender pigments (D) to be used include silicone powders, silicone elastic powders, polyurethane powders, cellulose powders, nylon powders, silk powders, PMMA powders, starch powders, polyethylene powders, polystyrene powders, metal soap powders such as zinc stearate, and complexes thereof. From the viewpoint of usability, an elastomer powder such as a silicone elastic powder and a polyurethane powder can be suitably used. A content of the organic extender pigment is preferably 1 to 10% by mass based on the total amount of the powder cosmetic.

The powder cosmetic of the present invention nay contain an oily component (E) which is usually used in a cosmetic. Examples of such oily components include naturally derived oils or waxes such as macadamia oil, avocado oil, corn oil, olive oil, rapeseed oil, sesame oil, castor oil, safflower oil, cottonseed oil, jojoba oil, coconut oil, palm oil, liquid lanolin, hydrogenated coconut oil, hydrogenated oil, Japan wax, hydrogenated castor oil, beeswax, candelilla wax, carnauba wax, insect wax (Ericerus pela), lanolin, hydrogenated lanolin, lanolin wax, and jojoba wax; hydrocarbons such as liquid paraffin, squalane, pristane, ozokerite, paraffin, ceresin, petrolatum, and microcrystalline wax; higher fatty acids such as oleic acid, isostearic acid, lauric acid, myristic acid, palmitic acid, stearic acid, behenic acid and undecylenic acid; higher alcohols such as cetyl alcohol, stearyl alcohol, isostearyl alcohol, behenyl alcohol, octyldodecanol, myristyl alcohol, and cetostearyl alcohol; synthetic ester oils such as cetyl isooctanoate, isopropyl myristate, hexyldecyl isostearate, diisopropyl adipate, di-2-ethylhexyl sebacate, cetyl lactate, diisostearyl malate, ethylene glycol di-2-ethylhexanoate, neopentyl glycol dicaprate, glycerin di-2-heptyl undecanoate, triethylhexanoin, trimethylolpropane tri-2-ethylhexanoate, trimethylolpropane triisostearate, and pentaerythrityl tetra-2-ethylhexanoate; silicone oils such as linear polysiloxanes such as dimethylpolysiloxane, methylphenylpolysiloxane, and diphenylpolysiloxane, cyclic polysiloxanes such as octamethylcyclotetrasiloxane, decamethylcyclopentasiloxane, and dodecamethylcyclohexasiloxane, and modified polysiloxanes such as an amino-modified polysiloxane, a polyether-modified polysiloxane, an alkyl-modified polysiloxane, and a fluorine-modified polysiloxane; and the like.

A content of the oily component to be blended is preferably 1 to 30% by mass relative to the whole amount of the powder cosmetic. When the powder cosmetic is a solid powder cosmetic prepared by a compression-molding method or a slurry-filling method, the content of the oily component is preferably 3 to 30% by mass, particularly 5 to 15% by mass, based on the whole amount of the powder cosmetic. When the content of the oily component is excessively large, spreadability is liable to decrease.

In the present invention, the powder cosmetic may contain a surfactant separately from the oily component. The surfactant improves usability such as affinity to the skin and picking up with the puff when used. Examples of such surfactants include fatty acid soaps such as sodium laurate and sodium palmitate; anionic surfactants such as potassium lauryl sulfate, and alkyl sulfate triethanol amine ethers; cationic surfactants such as stearyl trimethylammonium chloride, benzalkonium chloride, and lauryl amine oxide; amphoteric surfactants such as imidazoline-based amphoteric surfactants (such as 2-cocoil-2-imidazolinium hydroxide-1-carboxyethyloxy disodium salt), betaine-based surfactants (such as alkylbetaine, amidobetaine, and sulfobetaine), and acylmethyltaurine; nonionic surfactants such as sorbitan fatty acid esters (such as sorbitan monostearate and sorbitan sesquioleate); glycerin fatty acids (such as glycerol monostearate); propylene glycol fatty acid esters (such as propylene glycol monostearate); and hydrogenated castor oil derivatives, glycerol alkyl ether, POE sorbitan fatty acid esters (such as POE sorbitan monooleate and polyoxyethylene sorbitan monostearate), POE sorbitol fatty acid esters (such as POE-sorbit monolaurate), POE glycerol fatty acid esters (such as POE-glycerol monoisostearate), POE fatty acid esters (such as polyethylene glycol monooleate and POE distearate), POE alkyl ethers (such as POE-2-octyldodecyl ether), POE alkyl phenyl ethers (such as POE nonylphenyl ether), Pulronic type polymers which are block polymers of POP and POE (Pulronic is a trademark owned by BASF), POE, POE-POP alkyl ethers (such as POE-POP-(2-decyltetradecyl) ether), tetronics, POE castor oil or hydrogenated castor oil derivatives (such as POE castor oil and POE hydrogenated castor oil), sucrose fatty acid esters, and alkyl glucosides. Among them, lipophilic nonionic surfactants having an HLB of 7 or less are preferably used. A content of the surfactant is 0.1 to 3% by mass based on the mass of the powder cosmetic.

In the powder cosmetic of the present invention, other optional ingredients which are usually used in cosmetics can be formulated within a range where the effect of the present invention are not essentially impaired. Examples of such optional ingredients include polyhydric alcohols such as polyethylene glycol, glycerin, 1,3-butylene glycol, erythritol, sorbitol, xylitol, maltitol, propylene glycol, dipropylene glycol, diglycerol, isoprene glycol, 1,2-pentanediol, 2,4-hexylene glycol, 1,2-hexanediol, and 1,2-octanediol; moisturizing components such as hyaluronic acid, sodium hyaluronate, sodium pyrrolidone carboxylate, lactic acid, and sodium lactate,; lower alcohols such as ethanol and isopropanol; vitamins such as vitamin A or its derivatives, vitamin B6 hydrochlorides, vitamin B6 tripalmitate, vitamin B6 dipalmitate, vitamin B2 or its derivatives, vitamin B12 or its derivatives, vitamin B15 or its derivatives, Vitamin E or its derivatives such as alpha-tocopherol, beta-tocopherol, gamma-tocopherol and vitamin E acetate, vitamin D or its derivatives, Vitamin H or its derivatives, pantothenic acid, pantethin, and pyrroloquinoline quinone.

Further, addition of an organic ultraviolet absorber such as a p-aminobenzoic acid-based ultraviolet absorber, an anthranilic acid-based ultraviolet absorber, a salicylic acid-based ultraviolet absorber, a cinnamic acid-based ultraviolet absorber, a benzophenone-based ultraviolet absorber, a sugar-based ultraviolet absorber, 2-(2'-hydroxy-5'-t-octylphenyl) benzotriazole, and 4-methoxy-4'-t-butyldibenzoylmethane enables to enhance a value of SPF or PA of the cosmetic.

The powder cosmetic for skin color correction of the present invention may be either powdery or solid. Examples of its use form include a control color, a face color, a blusher, a highlight, a foundation, a base powder, a finishing powder, a cheek color, an eye color, a waterpact, a two-way cake, and a body powder.

The powder cosmetic can be prepared by uniformly mixing the component (A), the component (B), and other components used as needed in accordance with conventional methods. The mixed powder may be filled into a container as it is and used as a loose powder. The mixed powder may also be filled into a container and pressed to form a solid powder. In the case of making the solid powder, after adding one or more volatile solvents selected from water, a lower alcohol, a volatile silicone, light liquid isoparaffin and the like to the mixed powder, it may be pressed and dried.

EXAMPLE

Hereinafter, the present invention will be described more specifically with reference to Examples and Comparative Examples, but the present invention is not limited by these examples. In the following description, an amount of each ingredient in the formulations is expressed in % by mass with respect to the whole composition unless otherwise indicated.

Examples 1 to 2 and Comparative Examples 1 to 3

Control Color

A control color of the formulation shown in Table 1 was prepared according to the following production procedure. Using a color meter (Color and Whiteness Meter NW-12 manufactured by Nippon Densyoku Industries Co., Ltd.), appearance color ($L^*$, $a^*$, $b^*$, $c^*$ and hue value H of Munsell) and its coating color ($L^*$, $a^*$, $b^*$, $C^*$ and hue value H of Munsell) were measured to determine a hue difference value ($\Delta H^*$) between an appearance color and a coating color. The results are shown in Table 1.

Production Procedure (1) Components 1 to 12 were mixed.
(2) Components 13 to 15 were added to the mixture of components 1 to 12 and mixed.
(3) The mixture of components 1 to 15 prepared in (2) above was filled in a metal pan and press-molded to obtain a control color.

TABLE 1

|   | Component | Example 1 | Example 2 | Comparative Example 1 | Comparative Example 2 | Comparative Example 3 |
|---|---|---|---|---|---|---|
| 1 | Red No. 226 | 0.06 |  | 0.06 | 0.06 |  |
| 2 | Aluminum lake of Yellow No. 4 (Dye content of 26%) |  | 0.09 |  |  |  |
| 3 | Red iron oxide |  |  |  |  | 1.00 |
| 4 | Titanium dioxide |  |  |  |  | 3.00 |
| 5 | Titanium dioxides-coated synthetic mica (green interference color) ※1 | 24.00 |  |  |  | 24.00 |
| 6 | Titanium dioxide-coated mica (violet interference color) ※2 |  | 24.00 |  |  |  |
| 7 | Titanium dioxide-coated synthetic mica (green interference color) ※3 |  |  | 24.00 |  |  |
| 8 | Prussian blue-coated (titanium dioxide-coated mica) ※4 |  |  |  | 24.00 |  |
| 9 | Spherical silica | 3.00 | 3.00 | 3.00 | 3.00 | 3.00 |
| 10 | Synthetic fluorphlogopite | 10.00 | 10.00 | 10.00 | 10.00 | 10.00 |

TABLE 1-continued

|   | Component | Example 1 | Example 2 | Comparative Example 1 | Comparative Example 2 | Comparative Example 3 |
|---|---|---|---|---|---|---|
| 11 | Urethane powder | 2.00 | 2.00 | 2.00 | 2.00 | 2.00 |
| 12 | Isostearyl sebacate-treated talc | 52.44 | 52.41 | 52.44 | 52.44 | 48.50 |
| 13 | Triethylhexanoin | 6.00 | 6.00 | 6.00 | 6.00 | 6.00 |
| 14 | Shea butter | 2.00 | 2.00 | 2.00 | 2.00 | 2.00 |
| 15 | Phenoxyethanol | 0.50 | 0.50 | 0.50 | 0.50 | 0.50 |
|   | Total | 100.00 | 100.00 | 100.00 | 100.00 | 100.00 |
|   | Evaluation | | | | | |
|   | Apparence color | | | | | |
|   | L* value | 91.36 | 97.93 | 78.92 | 64.64 | 66.14 |
|   | a* value | 26.92 | 0.35 | 29.49 | 8.04 | 24.35 |
|   | b* value | 3.7 | 15.26 | 3.03 | 9.49 | 23.89 |
|   | Hue value H (Munsell) | 1.5R | 1.4Y | 1.1R | 9.7R | 8.9R |
|   | Chroma (C*) | 27.17 | 15.26 | 29.65 | 12.44 | 34.11 |
|   | Coating color | | | | | |
|   | L* value | 61.72 | 62.31 | 57.84 | 60.42 | 61.77 |
|   | a* value | -2.28 | 4.27 | 2.1 | -2.15 | 6.54 |
|   | b* value | 1.93 | -6.87 | 0.21 | 4.08 | 13.04 |
|   | Hue value H (Munsell) | 9.9GY | 3.6P | 1R | 2GY | 3.2YR |
|   | Chroma value (C*) | 2.99 | 8.09 | 2.12 | 4.61 | 14.58 |
|   | Hue difference value between appearance color and coating color) (ΔH*) | 16.46 | 21.3 | 0.51 | 8.47 | 7.33 |

※1 Product name: Topy Industries, Helios R20G
※2 Product name: BASF, Flamenco Violet 520C
※3 Product name: Topy Industries, Helios R100G
※4 Product name: BASF, Croisone Green
C* = 12.67, Particle diameter = 21 μm
C* = 16.95, Particle diameter = 25 μm
C* = 4.59, Particle diameter = 100 μm
C* = 11.54, Particle diameter = 25 μm As seen from the results of Table 1, the control color of Example 1 using a green interference pigment with a chroma C* value of 12.67 had an appearance color having a hue value H in Munsell color system of 1.5R that means redness and a coating color having a hue value H in Munsell color system of 9.9GY that means yellowish green. A hue difference value ΔH* of the control color is 16.46 that demonstrates that the appearance color is clearly different from the coating color. The control color of Example 2 using a violet interference pigment with a chroma C* value of 16.95 had a clear difference between its appearance color and its coating color (that is, hue difference value ΔH* of 21.3), since the appearance color is yellow, and the coating color is violet. On the other hand, the control color of Comparative Example 1 using titanium dioxide-coated synthetic mica (green interference pigment) having a chroma C* value of 4.59 had a smaller difference value ΔH* compared with that of the control color of Example 1, and no clear color change was observed between its appearance color and its coating color. The control color of Comparative Example 2 using Prussian blue-coated (titanium dioxide-coated mica) as an interference pigment had a hue difference value ΔH* of 8.47 meaning that a difference in hue between its appearance color and its coating color is small. The control color of Comparative Example 3, in which a content of the color pigment is 4% by mass, had a hue difference value ΔH* of 7.33 meaning that a difference in hue between its appearance color and its coating color is small.

INDUSTRIAL APPLICABILITY

The powder cosmetic of the present invention has an appearance color different from its coating color, is excellent in aesthetic effect and correction effect to natural skin color, and is suitably used for skin color correction.

What is claimed is:
1. A powder cosmetic, comprising:
    3 to 80% by mass of a colorless interference pigment having a chroma C* value of 5.0 or more (A), and
    0.005 to 2% by mass of an organic color pigment (B) having a color tone different from the interference color of the colorless interference pigment (A),
    wherein a hue difference value ΔH* between an appearance color and a coating color is 10 or more.
2. The powder cosmetic according to claim 1, wherein the hue difference value ΔH* is 15 or more.
3. The powder cosmetic according to claim 1, further comprising an inorganic extender pigment (C) in a content of 40 to 96% by mass.
4. The powder cosmetic according to claim 3, wherein the component (C) is a surface-hydrophobized pigment.
5. The powder cosmetic according to claim 1, further comprising an organic extender pigment (D) in a content of 1 to 30% by mass.
6. The powder cosmetic according to claim 1, further comprising an oily component (E) in a content of 1 to 30% by mass.
7. The powder cosmetic according to claim 1, wherein an average particle diameter of colorless interference pigment (A) is 21-300 μm.
8. The powder cosmetic according to claim 1, further comprising 1 to 10% by mass of an organic extender pigment (D).
9. The powder cosmetic according to claim 1, wherein the organic color pigment (B) comprises Red No. 201, Red No. 202, Red No. 226, Yellow No. 205, Yellow No. 401, Blue

No. 404, aluminum lake of Yellow No. 4, aluminum lake of Yellow No. 5, or aluminum lake of Blue No. 1.

10. The powder cosmetic according to claim 3, wherein inorganic extender pigment (C) comprises synthetic phlogopite, boron nitride, sericite, or synthetic mica.

11. The powder cosmetic according to claim 3, wherein inorganic extender pigment (C) comprises isostearyl sebacate-treated talc.

12. The powder cosmetic according to claim 5, wherein the organic extender pigment (D) comprises a silicone powder, a silicone elastic powder, or a polyurethane powder.

13. The powder cosmetic according to claim 1, comprising:
- 40 to 96% by mass of an inorganic extender pigment (C) comprising synthetic fluorophlogopite;
- 1 to 10% by mass of an organic extender pigment (D) comprising a polyurethane powder; and
- 1 to 30% by mass of an oily component (E) comprising triethylhexanoin.

14. A powder cosmetic, comprising:
- 3 to 80% by mass of a colorless interference pigment having a chroma $C^*$ value of 5.0 or more (A), and p1
- 0.005 to 2% by mass of an organic color pigment (B) having a color tone different from the interference color of the colorless interference pigment (A), wherein a hue difference value $\Delta H^*$ between an appearance color and a coating color is 10 or more, and wherein the powder cosmetic has an appearance color having a similar color tone to that of a skin trouble, while the interference pigment provides an interference color that corrects the color tone of the skin trouble.

15. A powder cosmetic, comprising:
- 3 to 80% by mass of a colorless interference pigment having a chroma $C^*$ value of 5.0 or more (A), and
- 0.005 to 2% by mass of an organic color pigment (B) having a color tone different from the interference color of the colorless interference pigment (A), wherein a hue difference value $\Delta H^*$ between an appearance color and a coating color is 10 or more and a color tone of the powder cosmetic before use is different from the color tone of a cosmetic film when applied to the skin.

* * * * *